(12) United States Patent
Sivathanu et al.

(10) Patent No.: US 6,184,989 B1
(45) Date of Patent: Feb. 6, 2001

(54) LASER SHEET TOMOGRAPHY APPARATUS FOR FLOW FIELD STATISTICS

(75) Inventors: Yudaya R. Sivathanu; Rony K. Joseph, both of W. Lafayette, IN (US)

(73) Assignee: En'Urga, Inc., W. Lafayette, IN (US)

( * ) Notice: Under 35 U.S.C. 154(b), the term of this patent shall be extended for 0 days.

(21) Appl. No.: 09/299,438

(22) Filed: Apr. 26, 1999

(51) Int. Cl.[7] .......................... G01N 21/59; G01N 21/85
(52) U.S. Cl. ............................................................ 356/437
(58) Field of Search .................................. 356/432, 437, 356/438, 439, 128, 129

(56) References Cited

U.S. PATENT DOCUMENTS 5,363,198 * 11/1994 Fournier ................................ 356/438
5,570,181 * 10/1996 Yasuo et al. ......................... 356/336
5,798,840 * 8/1998 Beitung ................................. 356/437

* cited by examiner

Primary Examiner—Richard A. Rosenberger
(74) Attorney, Agent, or Firm—Locke Reynolds LLP

(57) ABSTRACT

Laser sheet tomography is employed to determine flow field statistics in non-steady and steady flow at high repetition rates. The laser sheet tomography system is divided into two independent optical portions, the laser illuminator and the laser imager. As an absorption instrument, the laser illuminator can be shone directly into the laser imager, or if desired, the two portions can be positioned orthogonally to each other with the laser imager observing the scattered light. The observed light is correlated with known variations in laser intensity of the imager to generate transmittance data from which asymmetry ratios and probability density functions of local absorption coefficients can be computed at time repetition rates of 200 Hz and greater.

22 Claims, 9 Drawing Sheets

Figure 1. Schematic of the absorption tomography equipment.

Figure 2. Matrix Spot Diagram

Instantaneous transmission across a turbulent flow.

Mean and RMS of transmission from a symmetric turbulent flow.

Geometry for projection transmittance measurements

LASER SHEET TOMOGRAPHY APPARATUS FOR FLOW FIELD STATISTICS

BACKGROUND OF THE INVENTION

The present invention relates generally to instruments and methods for measuring flow characteristics, particularly of particulate bearing gases, in a non-invasive manner. The invention pertains particularly to optical tomography of a number of parallel linear elements defining a plane or sheet arranged generally orthogonally with respect to the direction of the flow of the gas in question.

It is desirable in a wide variety of circumstances to measure the characteristics of a flow of gas, particularly one bearing discrete particles within the flow. For example, it is desirable in some circumstances to monitor the particulate content in smokestacks and powder processing plants. It is desirable in other circumstances to measure the total mass flux of particulates in gas streams in some industries, for example, pharmaceutical industries. The information desired includes information on radial and circumferential inhomogeneities in flows such as sprays and particulate laden flows. An example of an area of particular interest is the physical characteristics providing information on the unmixedness of fuel and air in premixed combustors. This information is useful for controlling combustor instability in premixed combustion. Applications include premixed natural gas turbines, automotive engines and power plant combustors. Finally, it is desirable to determine the probability density functions of local absorption coefficients in research applications related to gas flows.

The measurement of such characteristics and the computation of such functions is not simple since the dynamic character of the flow itself results in rapid changes in flow conditions. Thus, it becomes desirable to measure the flow characteristics over a spatial area incorporating at least a substantial portion of the total flow being studied. It is also desirable to measure the flow characteristics repeatedly as a function of time so that the dynamic character of the flow can be faithfully reflected in the measurements of the asymmetry of the flow as well as the probability density functions of local extinction coefficients.

To obtain the probability density functions of local extinction coefficients, three different techniques are available from the prior art. A first technique is based on the discrete probability function method as described in a paper by Y. R. Sivathanu and J. P. Gore (1993), "A Tomographic Method for the Reconstruction of Local Probability Density Functions," *J. Quant. Spec. & Rad. Trans.*, vol. 50, pp. 483–492. A second method is based on Fourier transform of the moments of the measured transmittances as described a paper by M. R. Nyden, P. Vallikul, and Y. R. Sivathanu (1996), "Tomographic Reconstruction of the Moments of Local Probability Density Functions in Turbulent Flow Fields," *J. Quant. Spec. & Rad. Trans.*, vol. 55, pp. 345–356. These two methods require a much longer time for obtaining the local probability density function than is desirable or even available in many of the circumstances outlined previously. A third method based on the image reconstruction algorithm of Vardi and Lee (1992) is preferable for much faster time response. However, this algorithm has so far not been used in the field of turbulent flow deconvolution.

Intrusive probe methods of measuring inhomogeneities in the flow are disclosed in a paper by Dibble, R. W., Chen, J. Y, and Mongia, R. K., 1997, "Optical Probe for Measuring the Extent of Air/Fuel Mixing in Premixed Combustion Turbines," Poster P2, Proceedings of the Annual Program Review Meeting: Advanced Turbine Systems, FETC, Morgantown, WV. However, for obtaining full flow field information, a large number of these probes have to be used making them impractical as full flow field in-homogeneity sensors. Additionally, the presence of the probes themselves contributes changes to the gas flow that in most circumstances is undesirable.

Optical absorption tomography instruments are disclosed in U.S. Pat. No. 4,386,854 and No. 5,798,840. The devices use a fan of laser light and a ring of detectors arranged in a circle to obtain multiple slices though the flow in question. However, the devices are not practical for application in many circumstances since it is often difficult to achieve a ring of detectors around a flow without substantial modification to the flow apparatus, or disturbance of the flow itself. In addition, deconvolution of the absorption data using a ring of detectors is very difficult and thus the repetition rate of such a fan beam tomography system for flow field inhomogeneities is undesirably low. Further, the fiber-optic fan-beam sources employed to illuminate the sample flow typically have a Gaussian distribution of energy across the beam that is undesirable since the signal incident on the detector pixels in the ring array varies from the center to the outermost edge of the beam. If not corrected, this distribution of energy effectively prohibits the amplification of the multiplexed signal from the array since such amplification can easily result in saturating the signal from the center pixel. This distribution of energy, if not corrected, also requires that the signal from the edge have a lower signal to noise ratio. While it has been suggested to smooth this distribution of energy through the use of variable neutral density filters positioned in front of the expanding fan-beam source, such filters have not achieved entirely desirable results. Since deconvolution techniques tend to build up errors towards the center, any variation in the distribution of energy across the beam will also seriously degrade the performance of the system.

U.S. Pat. No. 5,178,002 discloses means for obtaining the density and velocity of a flow field using absorption and/or laser induced fluorescence in conjunction with phase doppler anemometry. While there is a brief reference made to obtaining local extinction coefficient information using multiple transmitters and receivers followed by a tomographic technique, no details are provided. There is no appreciation that the absorption signal varies in time or that, for turbulent flows, tomography from instantaneous measurements would require multiple angles and multiple slices. Further the question of deconvolution of the turbulent flow fields which are not instantaneously axisymmetric has not been addressed at all. There is no disclosure of any use of any form of statistical deconvolution techniques for treatment of the data, or of the problems associated with such techniques. Nor is there any appreciation that the mean transmittance could be used to obtain mean absorption coefficients using conventional and well known non-statistical deconvolution techniques.

U.S. Pat. No. 4,986,654 describes a planar, laser-induced fluorescence method of obtaining time resolved local density and temperature measurements in a flame. This is accomplished by measuring the absorption of fluorescence radiation using multiple cameras to cover multiple angles. The holographic deconvolution technique of Radon transforms mentioned in the patent uses instantaneous absorption along several slices and several projections, and is prone to severe error as pointed out in the Sivathanu and Gore article and the Nyden et. al. article referenced above. Thus, it remains desirable to measure flow characteristics over a spatial area incorporating at least a substantial portion of a total flow being studied as a function of time so that the dynamic character of the flow can be faithfully reflected in the measurements of the asymmetry of the flow as well as the probability density functions of local extinction coefficients.

SUMMARY OF THE INVENTION

Laser sheet tomography is employed in the present invention to determine flow field statistics in non-steady and steady flow at high repetition rates. The laser sheet tomography system is divided into two independent optical portions, the laser illuminator and the laser imager. As an absorption instrument, the laser illuminator can be shone directly into the laser imager, or if desired, the two portions can be positioned orthogonally to each other with the laser imager observing the scattered light.

The laser illuminator comprises a fan laser source that is collimated using a plano-convex lens system to form a collimated sheet beam having a preselected width. The laser source produces a "top hat" profile for the beam, in contrast to the typical Gaussian beam profile used in the prior art, which provides a very even distribution across the entire plane of the laser sheet. As the collimated laser sheet passes through the flow, a part of the laser sheet is absorbed or scattered by the flow, while the remainder is focussed onto a linear diode array or a line scan camera.

One feature of the present invention is the use of a collimated "top-hat" profile laser beam as the source signal. The collimated "top-hat" profile laser beam has the advantage of providing a uniform signal to noise ratio across the entire signal field of parallel light paths thus simplifying the deconvolution of the absorbed or scattered signal field.

Another feature of the present invention is the use of a laser diode to generate the illumination signal. The use of a laser diode has the advantage of making the system very rugged and thus transportable. It has the added advantage of allowing easy synchronization of the illumination signal with the data collection whereby digital and analog lock-in-amplification techniques are easily implemented. In addition, the synchronous data collection eliminates unwanted environmental radiation. This eliminates the radiation emitted from flows, which is of importance when viewing fires or other high temperature flows.

Yet another feature of the present invention is the use of a laser illuminating and imaging system that provides matrix spot sizes that are less than the size of the pixels for most of the flow region. This is essential to prevent contamination of the absorption or scattered signal due to interaction between parallel light paths.

Still another feature of the present system is the use of a controller that has a universal serial bus controller in it. This has the advantage of allowing high-speed data transfer to a computer, which is not possible using standard parallel and serial port connections.

Another feature of the present system is the use of a unique algorithm to provide instantaneous asymmetry in flows at frequencies in excess of 200 Hz and preferably as high as 2000 Hz. This high frequency feature has the advantage of enabling on-line monitoring and control of flow field inhomogeneities.

Additionally, the present system has a unique iterative deconvolution algorithm that provides the probability density functions of local extinction coefficients based on these path-integrated measurements. This information is not possible to obtain in turbulent flows from current tomographic equipment which typically uses instantaneous shot images rather than the time averaged measurements techniques of the present invention followed by statistical deconvolution.

Additional features and advantages will become apparent to those skilled in the art upon consideration of the following specification, which when taken in conjunction with the drawings, sets forth the preferred embodiment of the present invention. The embodiment of the invention disclosed herein is the best mode contemplated by the inventors for carrying out the invention in a commercial environment, although it should be understood that various modifications can be accomplished within the parameters of the present invention.

DESCRIPTION OF THE PREFERRED EMBODIMENTS

Figure 1:
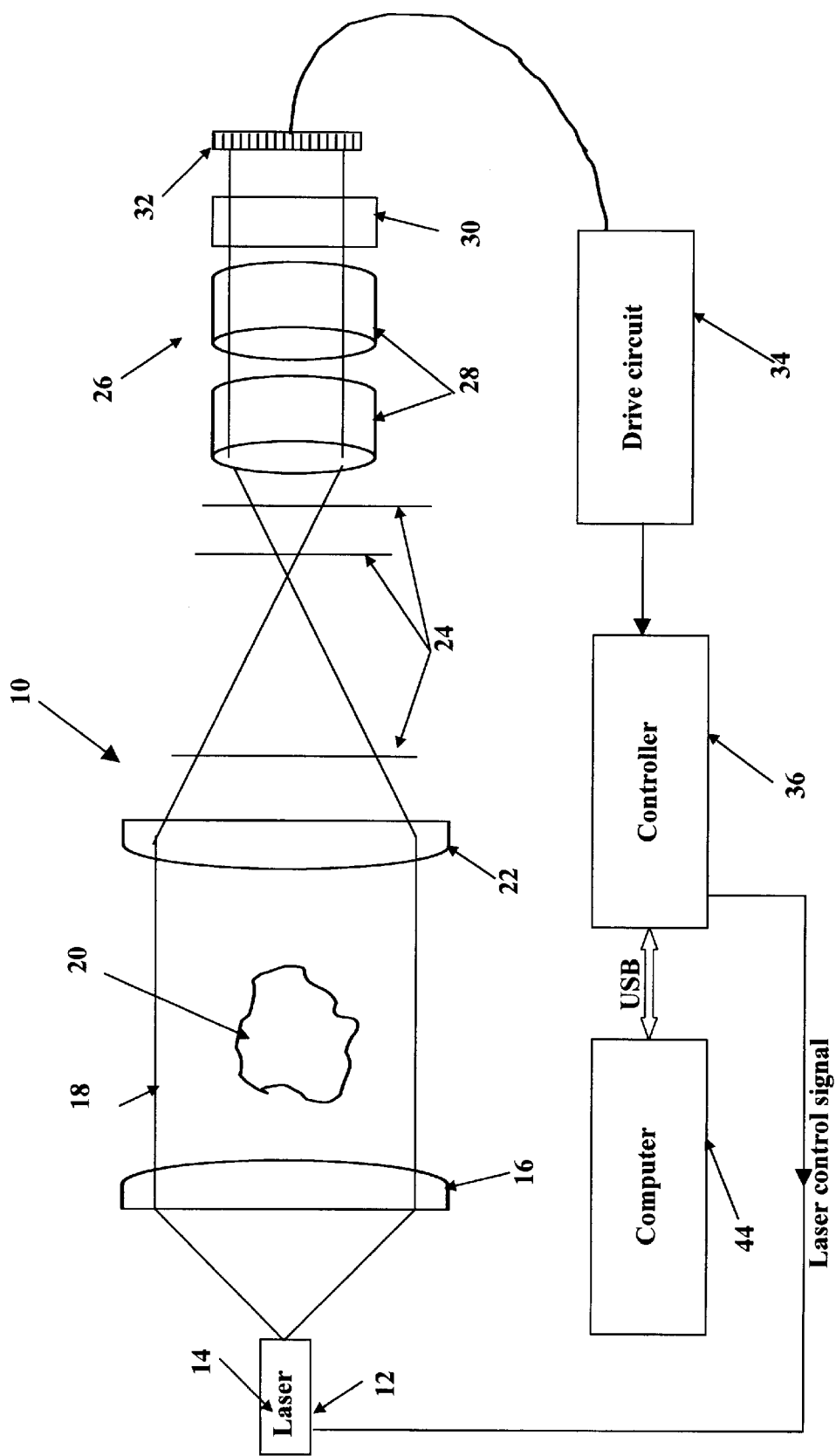
FIG. 1 is a block diagram of a laser sheet tomography apparatus of the present invention.

An optical tomography apparatus 10 of the present invention includes a laser illuminator 12 as shown in FIG. 1. The laser illuminator 12 includes a diode fan laser 14 such as LASIRIS Model No. SNF-501L-635S-5-30. Light emitted by the diode fan laser 14 is converted into a collimated sheet 18 using a plano-convex lens system 16 such as a Melles Griot Model No. 01 LPx281. A 635 nm diode laser is preferred for this application due to its low cost, small size and ruggedness. This laser system 14 includes optics that generate a 30 degree laser fan having a "top hat" beam profile, that is, a substantially uniform energy density across the entire beam. In the preferred embodiment, the laser beam is allowed to expand until it is about 10 cm wide, although further beam expansion might be possible with larger optics. The diameter of the lens system 16 determines the maximum diameter of the flow 20 that can be interrogated with this technique. That is, a 10 cm lens allows a flow diameter of 10 cm to be illuminated.

The collimated laser sheet 18, comprising a plurality of parallel rays of light, passes through the flow 20, such as a spray of premixed hydrocarbon fuel or a particulate-containing flow, and a part of the laser sheet 18 is absorbed or scattered by the spray or flow. A second plano-convex lens system 22 directs the light passing through the flow through apertures or stops 24 which restrict any widely scattered portion of the signal. The light then passes into an imaging lens system 26 including a doublet 28 for correcting any color divergence and a piano-concave lens system 30 to flatten the resulting image which is focussed onto a linear diode array 32 such as a Hamamatsu s3924-256Q, which has a light receiving surface defined by a 128×2 array of pixels that is 2.5 mm wide and 50 μm tall. It will be appreciated that other linear diode arrays or line scan cameras could be employed in the present invention particularly in circumstances where the composition of the flow under consideration demands the use of laser sources selected to avoid or employ certain specific wavelengths.

Figure 2:
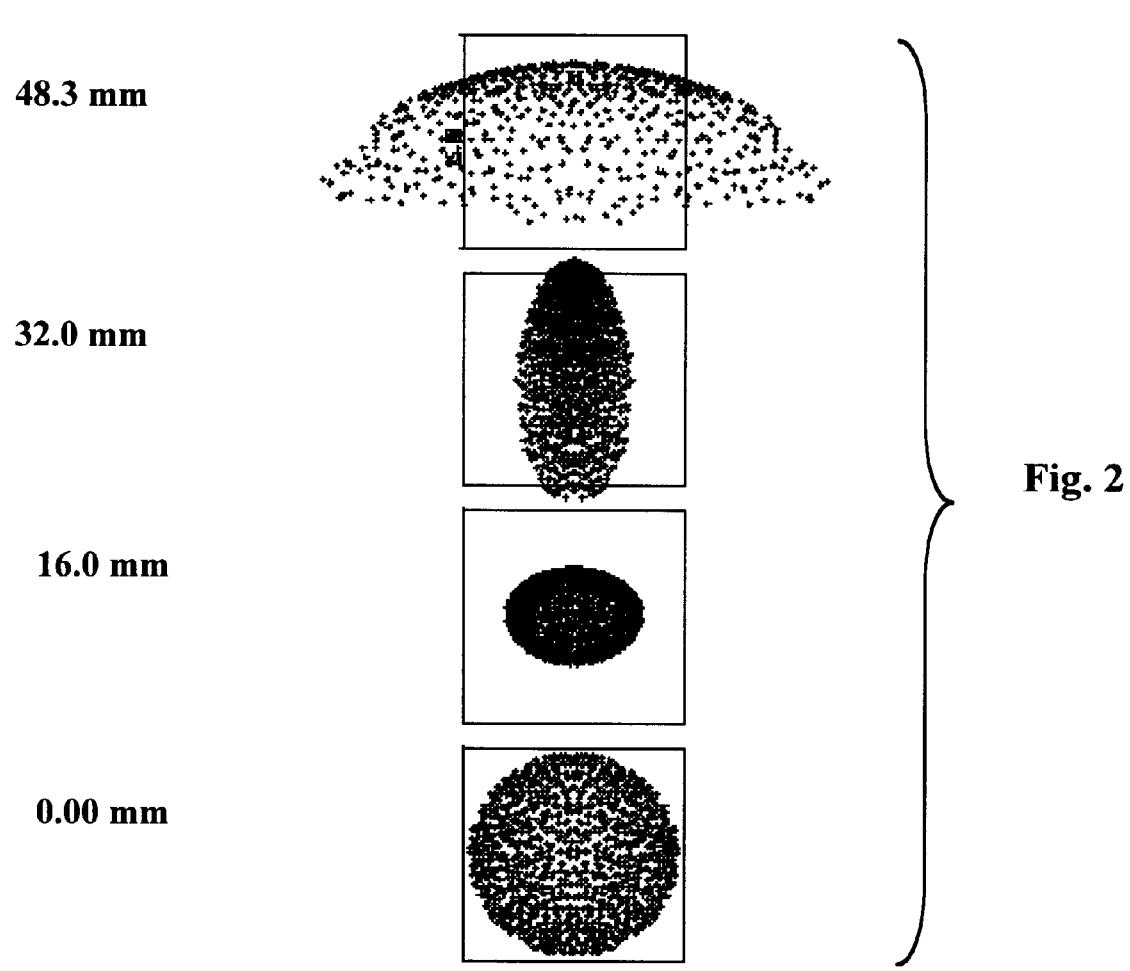
FIG. 2 is an illustration of the laser beam distributions in relation to the pixels of the diode array at various positions along the array.

The present laser illuminating and imaging system provides matrix spot sizes that are less than the size of the pixels for most of the flow region 18. This is essential to prevent contamination of the absorption signal due to interaction between the parallel light paths. FIG. 2 shows four diagrams of the dispersion of the light from single pixels forming the laser sheet beam at four different locations along the linear diode array 32. From the center of the laser beam to a distance of 32 mm from the center as measured at the light-receiving surface of the diode array 32, the spot dispersion is less than 25 microns providing for very high spatial resolution with substantially no light signal overlap between adjacent pixels. This is very important for deconvolution of local absorption since there should be no interference between laser beams passing through different paths in the flow.

The diode array 32 is connected to a drive circuit 34 such as a Hamamatsu Model C4091. The drive circuit 34 is connected to DC power supplies, not shown. On power up, the drive circuit 34 provides proper biasing and multiplexing of the signals from the linear diode array 32. In addition, the drive circuit 34 provides a multiplexed output signal $V_m$ from the array 32 that reflects the transmittance of the laser beam 18 through the area including the flow 20. The multiplexed voltage output $V_m$ from the array 32 is send to a controller 36.

Figure 3:
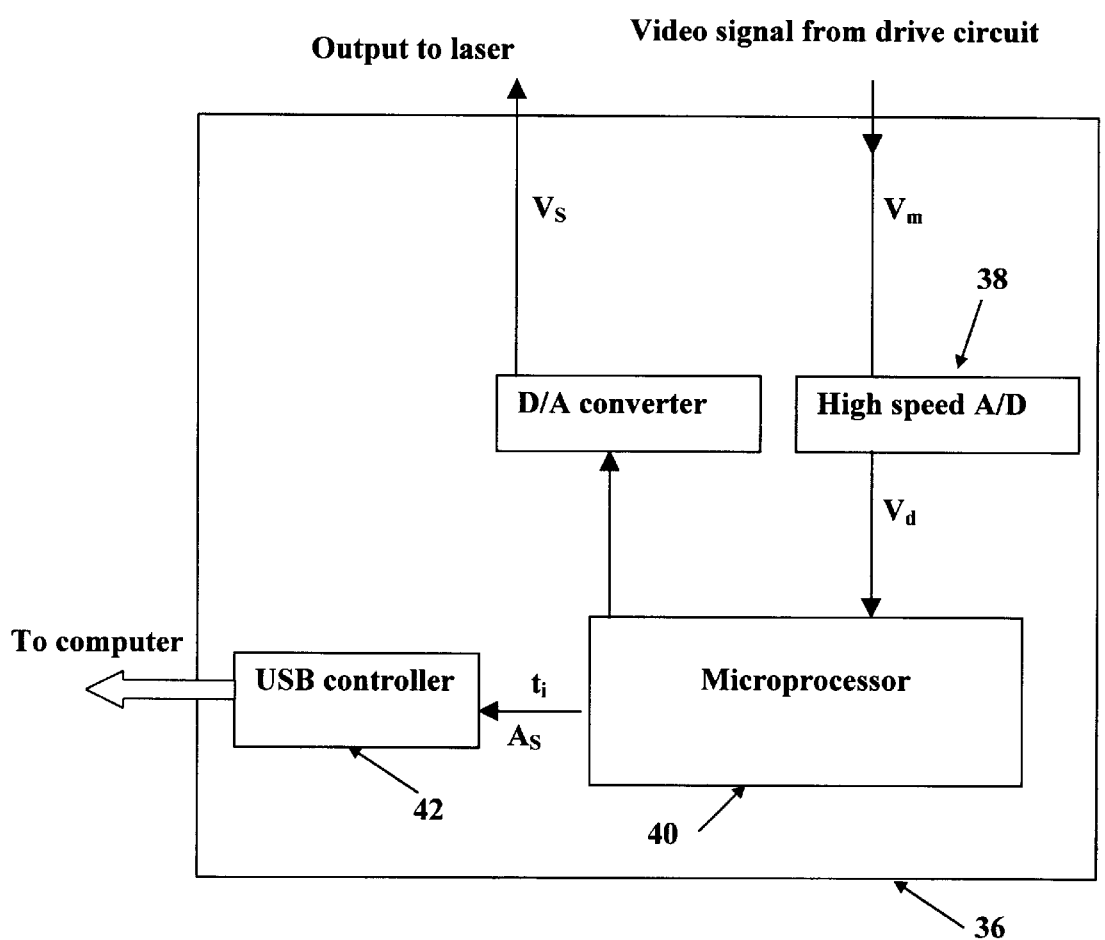
FIG. 3 is a block diagram of the controller shown in FIG. 1.

The controller 36 is shown in FIG. 3 to include a high speed analog to digital converter 38. The video output $V_m$ from the drive circuit 34 is converted to digital voltages $V_d$ using the high speed A/D converter 38. The controller 36 also includes a microprocessor 40, such as a Motorola PowerPC MPC 823, that takes a sample S of the digital video $V_d$ in synchronization with a sinusoidal modulation voltage $V_s$ supplied to the laser 14 that causes a corresponding sinusoidal output from the laser. The digital samples are obtained when the laser output is at a maximum and when the laser output is at a minimum. This difference in laser output provides a demodulated voltage $\Delta V$ derived from the output of the pixels of the diode array 32 which can be compared with a similarly demodulated reference voltage $\Delta V_o$ representing a clear path signal. The clear path signal can be taken from an end pixel of the array which is outside the flow area or can be taken from a separate detector (not illustrated) which receives a signal from the source by way of a path outside the sheet 18. For example, the separate detector could receive a signal from a beam splitter (not illustrated) inserted into at least a portion of the sheet before arriving at the region of the flow 20.

The ratio of the demodulated voltages $\Delta V/\Delta V_o$ for each pixel output is the transmittance τ of the path measured by each pixel. The transmittances τ are simultaneously yet separately computed for each of the parallel paths by sampling the entire pixel array 32 so that the entire sheet 18 can be then analyzed as a function of time to gain a picture of the flow 20 being measured. It will be appreciated that the synchronization of the laser 14 with the data collection enables the implementation of both digital and analog lock-in-amplification techniques. This eliminates any secondary or inherent radiation emitted from the flow 20, which is of importance when viewing fires or other high temperature flows. In addition, the synchronous data collection eliminates unwanted environmental radiation.

The frequency f of the sinusoidal voltage $V_s$ is at least at twice the frequency of interest in the flow. Since the signal S is grabbed only in synchronization with the maximum and minimum of the laser output, unwanted radiation emitted from the flow, which typically moves at less than half the frequency of the sinusoidal voltage, is eliminated. Typically, the frequency of interest in flow studies is determined by the particular aspect of the flow sought to be measured. For example, the turn-over time for large eddies or large scale mixing is typically much longer than the time for small scale mixing. Satisfactory pictures of even small events are generally capable of being captured at a frequency f of 200 Hz with increasingly fine detail being available at a frequency of 2000 Hz. In addition, the controller 36 includes a universal serial bus controller 42 that converts the data of each of the measured transmittances of each of the paths $\tau_i$ into USB protocol for high speed transfer to a computer 44 for storage or on-line analysis. This high speed data transfer to the computer 44 is not possible using standard parallel and serial port connections.

Two quantities of immediate interest that can be obtained using the laser sheet tomography of the present invention are the asymmetry of the flow as well as the probability density functions of local extinction coefficients.

Figure 4:
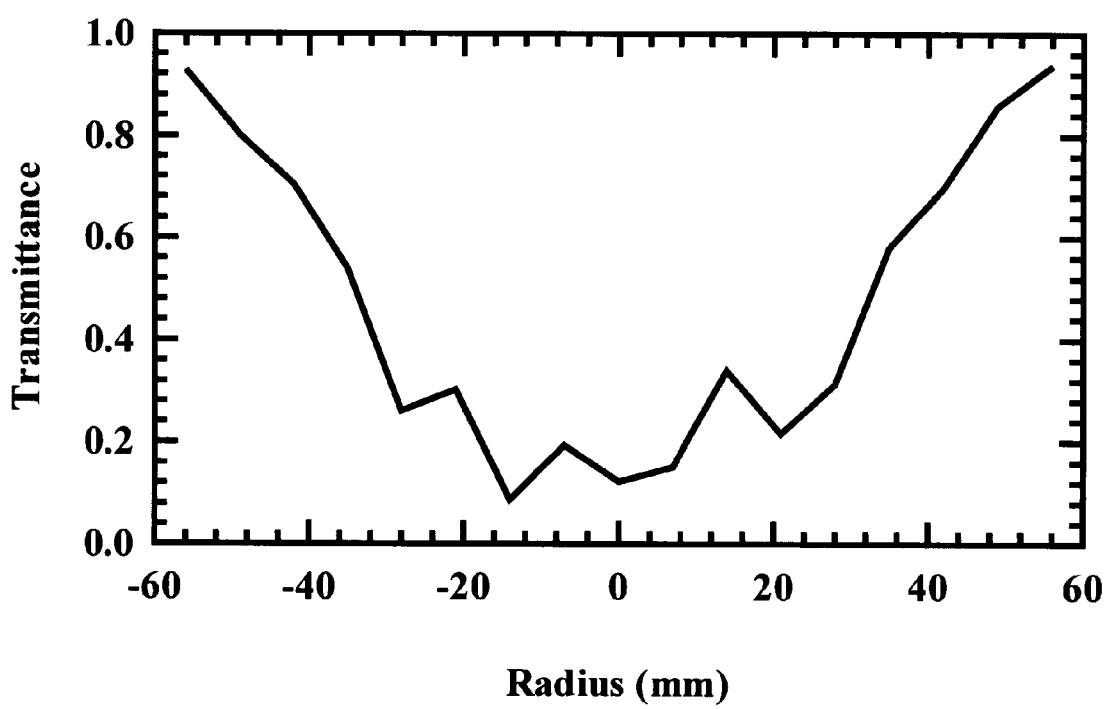
FIG. 4 is a graph of instantaneous transmission across a representative turbulent flow.
Figure 5:
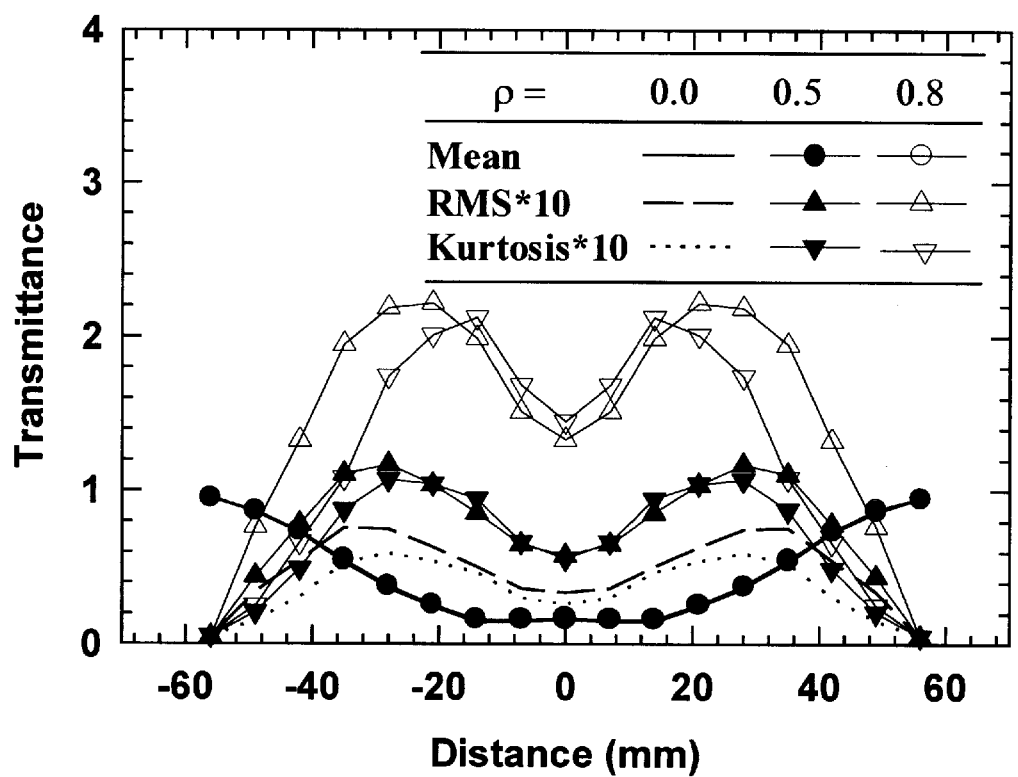
FIG. 5 is a graph of the mean and root mean square of the transmission from a symmetric turbulent flow for different levels of correlation (rule) between the rings.

The transmittance τ across the flow varies with time for an unsteady flow and is constant with time for a steady flow. A typical plot of the instantaneous transmittance τ across a flow is shown in FIG. 4. Since turbulent flows are instantaneously asymmetric, the transmittances measured across the linear array is not symmetric. Some statistical measurements of the transmittance τ across the flow are shown in FIG. 5. If the flow has no persistent asymmetry, then the mean and the RMS curves of transmission would be symmetric as shown in FIG. 5. However, if the flow has persistent asymmetry, then the mean and the RMS curves would be asymmetric. These asymmetries can be obtained from an average of as few as 50 readings in turbulent flows.

The disclosed invention provides the mean and RMS measures of transmittances τ across the flow as well as the asymmetry ratio, As, which is defined as:

$$A_S = \sum_{i=1}^{128} (\tau_i - \tau_{257-i})^2 \quad (1)$$

where $\tau_i$ is the transmittance measured at pixel i. This equation is just one representative form of asymmetry which uses the second moment. Other form of asymmetry such as using the first, third, forth or other moments is also possible Running averages of the average transmittances, RMS transmittances and the mean asymmetry ratios are provided at all times, by the microprocessor 40 of the disclosed invention. For equation (1), it is assumed that the center of the flow is aligned using a laser beam or other suitable optical method to the center of the laser sheet. If the center of the flow is not aligned with the center of the sheet, Equation (1) can be modified by shifting the pixel number to match the center of the flow. The asymmetry can be obtained very quickly using the microprocessor 40 which is capable of providing a running average of the asymmetry with an update provided at least every 10 msec. The present system uses an algorithm reflecting equation (1) to provide instantaneous asymmetry in flows at frequencies in excess of 200 Hz. This allows in many situations an on-line monitoring and control of flow field inhomogeneities.

Figure 6:
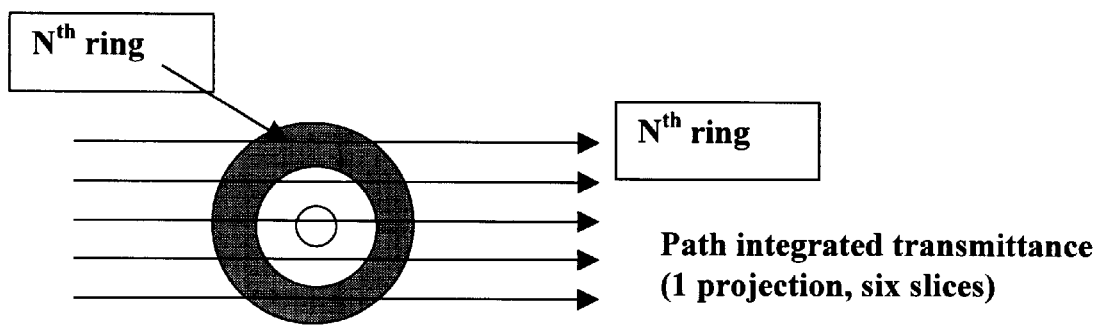
FIG. 6 is a diagram of the geometry for projection transmittance measurements.

The present system has an iterative deconvolution program resident in computer 44 that provides the probability density functions of local absorption coefficients based on these path-integrated measurements. The objective of the algorithm is to find the probability density function (PDF) of local properties from path integrated measurements. The geometry of a typical problem is as diagrammed in FIG. 6 illustrating in horizontal cross-section a turbulent flow issuing from a round nozzle. The probability density functions of path integrated transmittances are computed for one projection and several slices as shown in FIG. 6.

Figure 7:
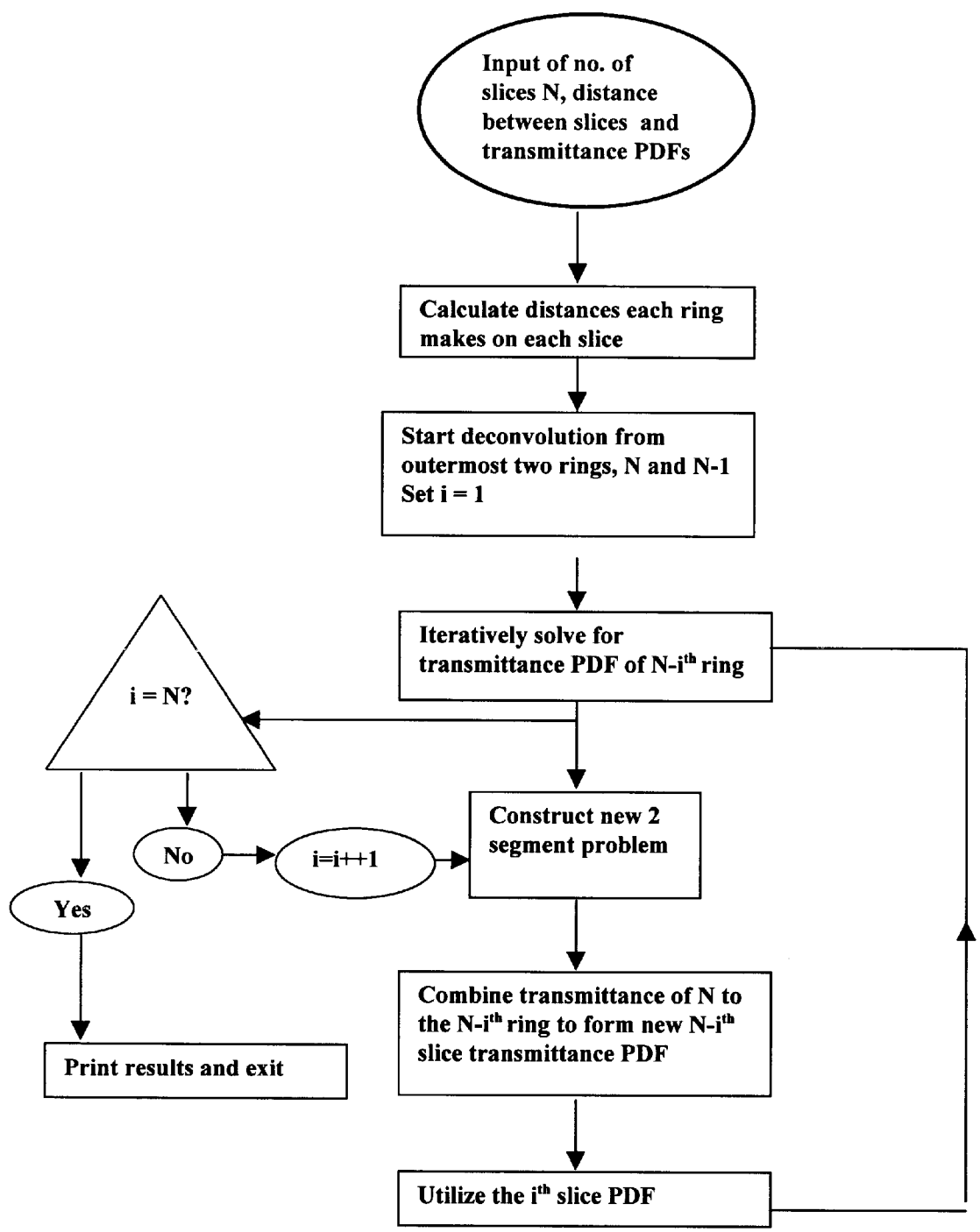
FIG. 7 is a flow chart of the onion peeling technique employed to compute the probability density functions of local properties from the path integrated transmittances.

The flow chart for the program is given in FIG. 7. The overall program follows a conventional onion peeling technique. The local transmittance PDF in each ring (N rings) is calculated starting from the outermost ring ($N^{th}$ ring). The transmittance PDFs from all the slices, number of slices (2*N−1), and the distance between the slices are used as input to the program. The program first calculates the length each ring occupies on every slice using standard geometrical equations. The transmittance PDF of the $N^{th}$ ring is first adjusted to account for the different length it occupies in the N−$1^{st}$ slice. The program next uses the transmittance PDFs of the last two slices ($N^{th}$ and N−$1^{st}$ slice) in an iterative algorithm to obtain the transmittance PDF of the N−$1^{st}$ ring. The program then provides the local transmittance PDFs of the N−1 ring.

The next step is to combine the transmittance PDF of the $N^{th}$ and the N−$1^{st}$ ring to form a new transmittance PDF of rings 1 and 2 on slice 3. This PDF along with the PDF of transmittance of slice 3 is considered as a new two segment problem, which is iteratively solved for the transmittance of ring 3.

The next step is to combine the transmittance PDF of the $N^{th}$, N−$1^{st}$, and N−$2^{nd}$ to form a new transmittance PDF of rings 1, 2 and 3 on slice 4. This PDF along with the PDF of transmittance of slice 4 is now the new two segment problem which is iteratively solved for the transmittance of ring 4. This procedure is repeated until the transmittance PDF of all the N rings are obtained.

Figure 8:
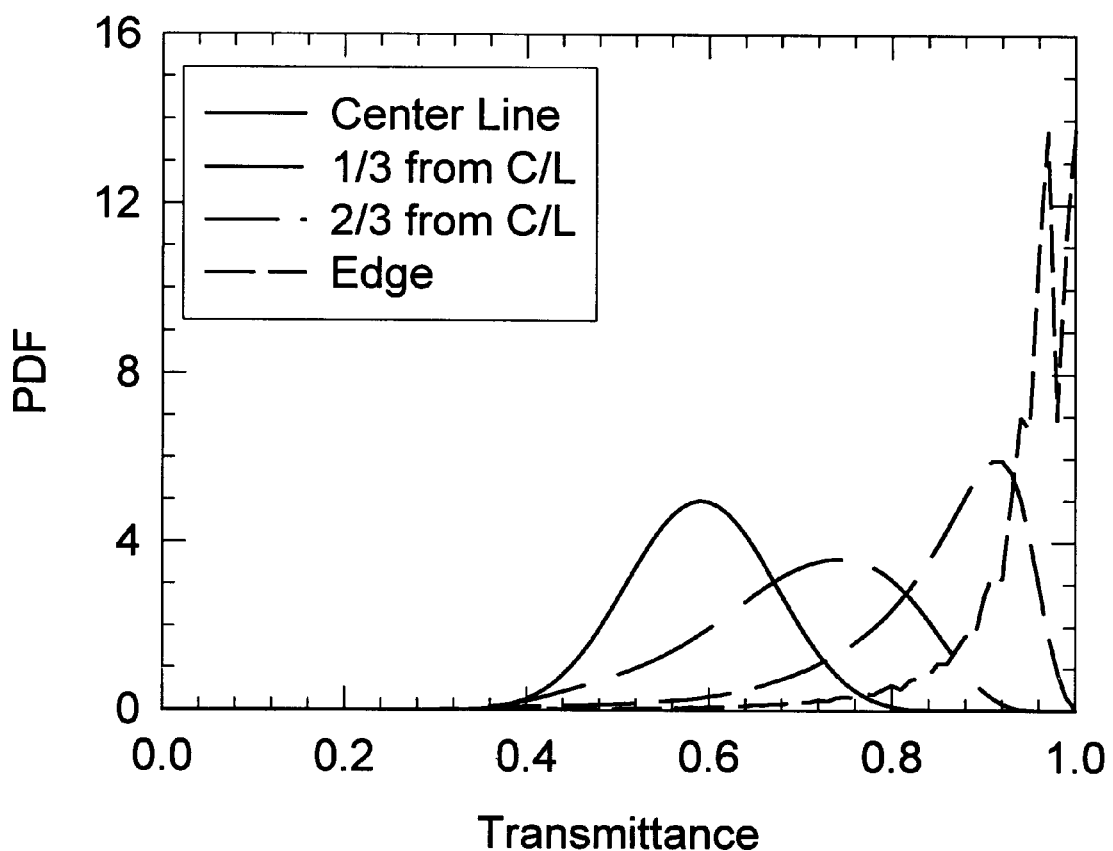
FIG. 8 is a graph of example probability density functions of path integrated transmittance for four paths.
Figure 9:
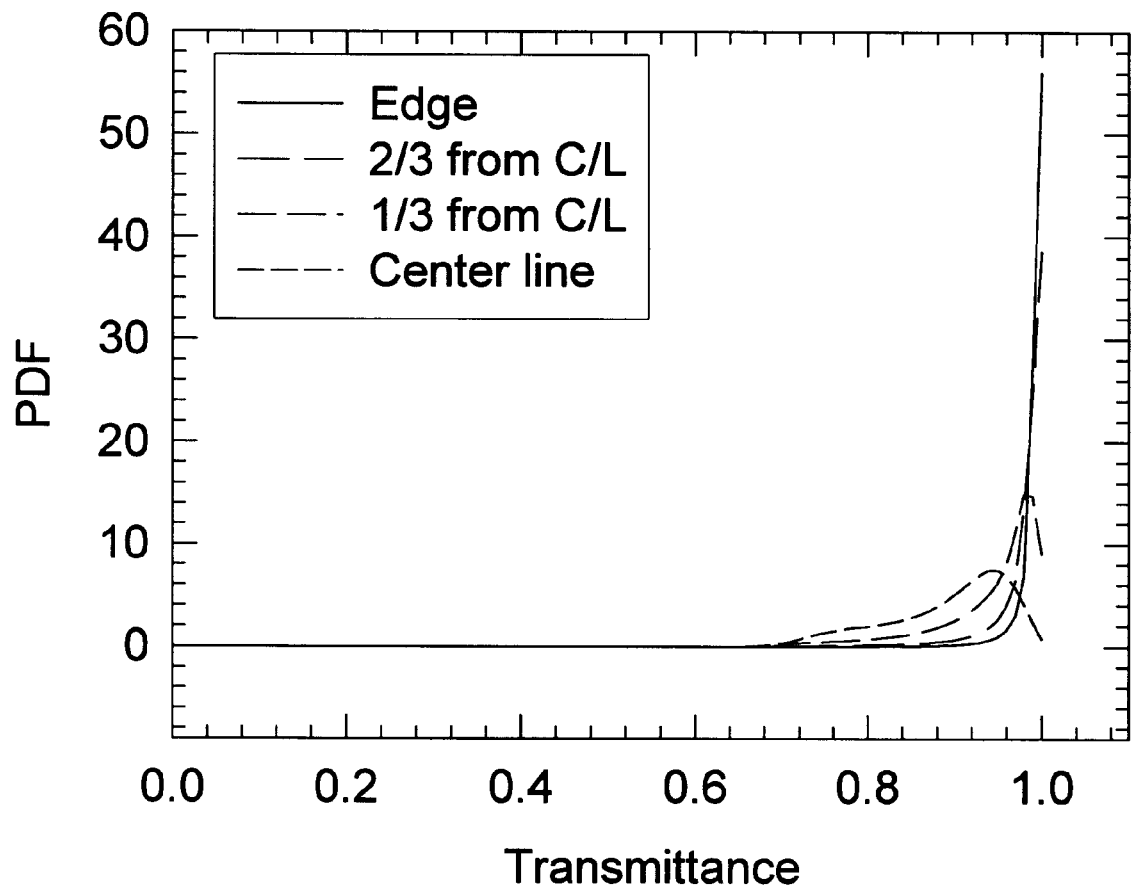
FIG. 9 is a graph of example probability density functions of local transmittance for four rings.

Typical PDFs of path integrated transmittances are shown in FIG. 8. PDFs of transmittances are shown for the center line of the flow, ⅓ distance from the C/L to the edge of the flow, ⅔ distance from the C/L to the edge of the flow and at the edge of the flow. It can be seen that the transmittance is progressively higher as we go towards the edges of the flow. Some sample PDFs obtained from the program are shown in FIG. 9.

The present system is capable of detecting flow field inhomogeneities. In some cases, when the inhomogeneities are asymmetric in a direction that is aligned to the laser sheet, a second laser beam tomography apparatus can be arranged at a different angle to detect the inhomogeneities. The choice of diode array 32 to be employed is in part a function of the expected use of the apparatus 10. For example, methane, which is the prime ingredient of natural gas, absorbs light at 3.39 microns. Therefore, using a laser diode at 3.39 microns and replacing the photo-diode array with a lead sulfide or lead selenide array, or any other infrared array, various characteristics including instantaneous inhomogeneities in fuel premixers can be obtained. In addition, the diode laser 14 can be synchronized with an external signal. This feature allows an effective frequency modulation of the laser beam 18 so as to eliminate unwanted radiation emission from the flow being illuminated.

An important feature of the preferred laser is the "top hat" profile of the beam in contrast to a Gaussian beam profile used in the prior art. This "top hat" profile provides a very even distribution across the entire laser sheet. This is crucial for obtaining the best possible signal to noise ratios. Gaussian beams when spread into a sheet have very low intensities at the edges of the sheet. This limits their application to very narrow flows. The present laser sheet tomography uses a laser illuminator and laser imager system to provide for parallel laser paths through the flow. This makes it possible to use standard deconvolution techniques that are well established and tested for steady flows.

The present invention having been described in its preferred embodiment, it is clear that the present invention is susceptible to numerous modifications and embodiments within the ability of those skilled in the art and without exercise of the inventive faculty. Accordingly, the scope of the present invention is defined as set forth by the scope of the following claims.

What is claimed is:

1. Apparatus for the non-invasive measurement of characteristics of a gas flowing through a plane within a defined region, the apparatus comprising:

a laser illuminator for generating laser radiation including a lens system for directing the radiation into said plane and through said defined region as a collimated sheet, a second lens system for collecting optical radiation traveling in said plane through said defined region, the second lens system having an optical output, an array of n rows of pixels, each row containing K pixels, the array being positioned with respect to the second lens system to receive the optical output of the second lens system and generating a voltage signal indicative thereof, and an analyzer coupled to the array of pixels for periodically sampling the voltage signal, the analyzer including computational capacity to compute statistical information relating to the voltage signal output from the array of pixels characteristic of said flowing gas as it passes through said plane, the analyzer including means for computing an asymmetry ratio, $A_s$, in accordance with the relation:

$$A_s = \sum_{i=1}^{K} (\tau_i - \tau_{nK+1-i})^2$$

where $\tau_i$ is the transmission measured at pixel i in a row of the array.

2. The apparatus of claim 1 wherein the laser illuminator generates a discrete set of parallel beams of laser radiation arranged in said plane, the beams being of substantially uniform energy density thereby defining said collimated sheet.

3. The apparatus of claim 1 wherein the second lens system is aligned with respect to the laser illuminator to receive the collimated sheet of laser radiation.

4. The apparatus of claim 1 wherein the array of pixels comprises a linear diode array situated with respect to the second lens system so that an edgewise image of said plane is focused across the entire linear diode array.

5. The apparatus of claim 1 further comprising a drive circuit coupled to the laser illuminator providing a periodic signal to the laser illuminator causing a periodic variation in intensity of the laser radiation generated thereby.

6. The apparatus of claim 5 wherein the drive circuit is coupled to said analyzer so that the periodic sampling of the voltage signal output from the array of pixels is synchronized with the periodic variation in intensity of the laser radiation emitted by the laser illuminator.

7. The apparatus of claim 1 wherein the analyzer includes a universal serial bus controller for converting the statistical information into USB protocol for high-speed transfer.

8. The apparatus of claim 1 wherein the analyzer includes means for computing probability density functions of local absorption coefficients based on path integrated measurements reflected in said output voltages.

9. The apparatus of claim 1 wherein the array of pixels is selected from a lead sulfide array or a lead selenide array.

10. The apparatus of claim 1 wherein the array of pixels consists of two rows, each row containing 128 pixels, and the asymmetry ratio, is computed in accordance with the relation:

$$A_S = \sum_{i=1}^{128} (\tau_i - \tau_{257-i})^2.$$

11. Apparatus for the non-invasive measurement of characteristics of a gas flowing through a plane within a defined region, the apparatus comprising:
   a laser illuminator for generating laser radiation including a lens system for directing the radiation into said plane and through said defined region as a collimated sheet,
   a second lens system for collecting optical radiation traveling in said plane through said defined region, the second lens system having an optical output,
   an array of n rows of pixels, each row containing K pixels, the array being positioned with respect to the second lens system to receive the optical output of the second lens system and generating a voltage signal indicative thereof,
   an analyzer coupled to the array of pixels for periodically sampling the voltage signal, the analyzer including computational capacity to compute statistical information relating to the voltage signal output from the array of pixels characteristic of said flowing gas as it passes through said plane, the analyzer including means for computing an asymmetry ratio, $A_s$, in accordance with the relation:

$$A_s = \sum_{i=1}^{K} (\tau_i - \tau_{nK+1-i})^2$$

where $\tau_i$ is the transmission measured at pixel i in a row of the array, and
   a drive circuit coupled to the laser illuminator providing a periodic signal to the laser illuminator causing a periodic variation in intensity of the laser radiation generated thereby, the drive circuit being coupled to the analyzer so that the periodic sampling of the voltage signal output from the array of pixels is synchronized with the periodic variation in intensity of the laser radiation emitted by the laser illuminator.

12. The apparatus of claim 11 wherein the laser illuminator generates a discrete set of parallel beams of laser radiation arranged in said plane, the beams being of substantially uniform energy density thereby defining said collimated sheet, the energy density periodically varying with time.

13. The apparatus of claim 12 wherein the second lens system is aligned with respect to the laser illuminator to receive the collimated sheet of laser radiation, the array of pixels comprising a linear diode array situated with respect to the second lens system so that an edgewise image of said plane is focused across the entire linear diode array.

14. The apparatus of claim 13 wherein the linear diode array is situated in optical linear alignment with the laser illuminator and further comprising a third lens system which focuses each of the discrete set of parallel beams to a corresponding pixel of the linear diode array with substantially no overlap between adjacent pixels.

15. The apparatus of claim 12 wherein the analyzer samples the voltage signal output from the array of pixels twice during each period of the periodic variation in intensity of laser radiation.

16. The apparatus of claim 11 wherein the array of pixels consists of two rows, each row containing 128 pixels, and the asymmetry ratio, is computed in accordance with the relation:

$$A_S = \sum_{i=1}^{128} (\tau_i - \tau_{257-i})^2.$$

17. A method for non-invasively measuring characteristics of a gas flowing through a plane within a defined region, the method comprising the steps of:
   directing laser radiation through a lens system into said plane and through said defined region as a collimated sheet,
   collecting optical radiation traveling in said plane through said defined region with a second lens system having an optical output,
   receiving the optical output of the second lens system with an array of n rows of pixels, each row containing K pixels, and generating a voltage signal indicative thereof,
   periodically sampling the voltage signal output from the array of pixels with an analyzer including computational capacity to compute statistical information relating to the voltage signal output with a characteristic of said flowing gas as it passes through said plane, and
   computing an asymmetry ratio, $A_s$, in accordance with the relation:

$$A_s = \sum_{i=1}^{K} (\tau_i - \tau_{nK+1-i})^2$$

where $\tau_i$ is the transmission measured at pixel i in a row of the array.

18. The method of claim 17 further comprising the steps of:
   providing a periodic drive signal to the laser illuminator to cause a periodic variation in intensity of the laser radiation generated thereby, and synchronizing the periodic sampling of the voltage signal output from the array of pixels with the periodic variation in intensity of the laser radiation emitted by the laser illuminator.

19. The method of claim 18 further comprising the step of:

sampling the voltage signal output from the array of pixels twice during each period of the periodic variation in intensity of laser radiation.

20. The method of claim 18 further comprising the step of:

computing probability density functions of local absorption coefficients based on path integrated measurements reflected in said output voltages.

21. The method of claim 20 further comprising the steps of:

partitioning the flow into a plurality of concentric rings of known dimension, calculating, for each parallel light path traversing the flow, the path length included in each of the rings, and step-wise deconvoluting the transmittance probability density functions of each ring starting with the outermost ring.

22. The method of claim 17 wherein the array of pixels consists of two rows, each row containing 128 pixels, and the asymmetry ratio, is computed in accordance with the relation:

$$A_S = \sum_{i=1}^{128} (\tau_i - \tau_{257-i})^2.$$

* * * * *